US006365380B2

(12) United States Patent
Liu et al.

(10) Patent No.: US 6,365,380 B2
(45) Date of Patent: Apr. 2, 2002

(54) METHOD FOR STEREOSELECTIVELY INVERTING A CHIRAL CENTER OF A CHEMICAL COMPOUND USING AN ENZYME AND A METAL CATALYST

(75) Inventors: Weiguo Liu, Buffalo Grove; Scott Laneman, Vernon Hills; David John Ager, Hoffman Estates; Paul Phillip Taylor, Arlington Heights, all of IL (US)

(73) Assignee: PCBU Services, Inc., Wilmington, DE (US)

( * ) Notice: Subject to any disclaimer, the term of this patent is extended or adjusted under 35 U.S.C. 154(b) by 0 days.

(21) Appl. No.: 09/766,762

(22) Filed: Jan. 22, 2001

Related U.S. Application Data

(62) Division of application No. 09/510,882, filed on Feb. 23, 2000, now abandoned.

(51) Int. Cl.$^7$ .................. C12P 13/04; C12P 13/22; C12P 13/08; C12P 13/06
(52) U.S. Cl. .................. 435/106; 435/108; 435/115; 435/116; 435/280
(58) Field of Search .................. 435/1.1, 106, 108, 435/115, 116, 280

(56) References Cited

U.S. PATENT DOCUMENTS

| | | | |
|---|---|---|---|
| 3,634,196 A | 1/1972 | Wagner et al. .............. | 435/229 |
| 3,849,252 A | 11/1974 | Percs et al. ................. | 435/214 |
| 4,889,804 A | 12/1989 | Schofield .................... | 435/155 |
| 5,135,860 A | 8/1992 | Anton et al. ................ | 435/136 |
| 5,364,797 A | 11/1994 | Olson et al. ................ | 436/501 |
| 5,728,555 A | 3/1998 | Fotheringham et al. ..... | 435/106 |
| 5,840,899 A | 11/1998 | Bedeschi et al. ............ | 546/48 |
| 5,922,183 A | 7/1999 | Rauh ........................ | 204/403 |

FOREIGN PATENT DOCUMENTS

| | | |
|---|---|---|
| EP | 0 135 846 A | 3/1985 |
| WO | WO 98/14602 A | 9/1998 |

OTHER PUBLICATIONS

Ager et al., "The Large Scale Synthesis of Unnatural Amino Acids", *Chimica OGGI/chemistry today,* vol. 15, No. 3–4 (1997).
International Search Report dated Nov. 29, 2001, in PCT/US01/05688.
Freimund et al., J. Carbohydrate Chemistry, 15(1), 115–120, 1996.*
Nitta et al., Journal of Bacteriology, vol. 117, No. 2, pp. 588–592, 1974.*
Registry File Citation, Chemical Abstracts, 2001.*
Sampath et al., *Anal. Chem.,* vol. 68, No. 13, 2015–2021 (1996).
Sampath et al., *Journal of Sol–Gel Science and Technology,* 7, 123–128 (1996).
Dragovich et al., *J. Org. Chem.,* vol. 60, p. 4922 (1995).
Ranu et al., *Tetrahedron Letters,* 35 (46), 8649 (1994).
Huh et al., Bio Sci. Biotech. Biochem., 56(12), 2081–82 (1992).
Huh et al., *J. Fermentation & Bioengineering* , 74(3), p. 189–190 (1992).
Balezewski et al., *J.A. Syn. Commun.,* vol. 20, p. 2815 (1990).
Barrett et al., *Tetrahedron Letters,* vol. 29, p. 5733 (1988).
Ram et al., *Tetrahedron Letters,* 29(31), 3741 (1988).
Johnstone et al., Chem. Rev., vol. 85, p. 129 (1985).
Hafner et al., Proc. Nat. Acad. Sci., (68)5, 987–91 (1971).

* cited by examiner

*Primary Examiner*—David M. Naff
*Assistant Examiner*—Mike Meller
(74) *Attorney, Agent, or Firm*—Marshall, Gerstein & Borun

(57) ABSTRACT

A process for stereoselectively inverting a chiral center of a chemical compound is disclosed. The process first consists of forming a mixture of the chemical comopund, an enzymatic system, and a metal catalyst. Next, the process stereoselectively dehydrogenates a group attached to the chiral center with the enzymatic system in the presence of an oxidant to produce a dehydrogenated group, Lastly, the process hydrogenates the dehydrogenated group with the metal catalyst in the presence of a hydrogen source to stereoselectively invert the chiral center of the chemical compound.

35 Claims, No Drawings

METHOD FOR STEREOSELECTIVELY INVERTING A CHIRAL CENTER OF A CHEMICAL COMPOUND USING AN ENZYME AND A METAL CATALYST

CROSS REFERENCE TO RELATED APPLICATION

This is a division of U.S. application Ser. No. 09/510,882 filed Feb. 23, 2000, now abandoned.

BACKGROUND OF THE INVENTION

1. Field of the Invention

The present invention relates to the production of chiral organic compounds via catalyzed reactions. More particularly, the present invention relates to a catalytic system that includes both a metal catalyzed hydrogen-transfer system and an enzyme or microbial catalyzed oxidation system, and a process of using this system for the production of optically active amino acids.

2. Brief Description of Related Technology

Traditional chemical catalysis generally refers to processes in which chemical reactions are catalyzed by acids, bases, metals, metal salts or organometallic compounds, while biocatalysis is used to describe reactions catalyzed by proteins, enzymes, other biomolecules, or microorganisms. Traditional chemical catalysis has long been used in the chemical industry for production of petro chemicals, fine chemicals, and specialty chemicals. Although fermentation has long been applied in the manufacture of certain commodity chemicals, more recently biocatalysis has focused on the production of high value fine chemicals, especially chiral chemical intermediates for pharmaceuticals, and other biologically active agents.

Each type of catalysis has its advantages and shortcomings. Traditional chemical catalysis generally involves high temperature, high pressure, and low chemical selectivity, but typically is cost effective and efficient. Biocatalysis works under mild reaction conditions with high chemical selectivity and stereoselectivity, but is usually associated with high cost. These two types of catalysis are usually applied in quite different processes and are rarely associated with each other. For example, catalytic transfer hydrogenation reactions have been used widely in the reduction of a variety of functional groups of organic compounds, such as the reduction of ketones and aldehydes (Ram S.; Spicer, L. D.; Tetrahedron Lett. 1988. 29(31). 3741), olefins (Ranu, B. C.; Sarkar, A.; Tetrahedron, Lett. 1994. 35(46), 8649), azides (Gartiser, T.; Selve, C.; Delpuech, J.-J.; Tetrahedron Lett. 1983, 24(15), 1609), epoxides (Dragovich, P. S.; Prins, T. J.; Zhou, R.; J. Org. Chem. 1995, 60, 4922), nitrates (Barrett, A. G. M.; Spilling, C. D. Tetrahedron Lett. 1988, 29, 5733), and aromatic rings (Balezewski, P.; Joule, J. A. Syn. Commun., 1990, 20, 2815).

A catalytic transfer hydrogenation system typically involves a metal or a metal-complex catalyst such as palladium-carbon, and a hydrogen source such as ammonium formate or cyclohexene. The hydrogen source releases hydrogen or hydride as the reaction proceeds. A major advantage over conventional catalytic hydrogenation, which requires special apparatus for handling hydrogen gas and pressure, is that the reduction is usually conducted under atomspheric pressure without large excess of hydrogen gas. Although there have been many different catalysts and hydrogen sources in catalytic transfer hydrogenation systems, an ammonium formate/palladium on carbon (Pd-C) system is the most versatile and practical catalytic hydrogen transfer agent, and has been used for the reduction of various functionalities (Johnstone, R. A. W.; Wilby, A. H.; Entwistle, I. D. Chem. Rev., 1985, 85, 129). To the best of our knowledge, however, the system has never been applied in combination with a biocatalytic system, or in the presence of biocatalysts such as enzymes or microorganisms.

With the exception of glycine, each of the common amino acids exists as one of two optical isomers, termed levorotatory or dextrorotatory, depending upon the direction in which they cause a plane of polarized light to rotate. By convention, amino acids are also referred to as D- or L- based upon whether the configuration about the α-carbon of the amino acid corresponds to the D- or L- stereoisomer (enantiomer) of glyceraldehyde, the arbitrary standard. Based upon that standard, most naturally-occurring amino acids are L-amino acids, despite that some of them are dextrorotatory when placed in aqueous solution at neutral pH.

On the other hand, amino acid oxidases and amino acid deaminases are classes of enzymes that catalyze the stereoselective oxidation of an amino acid to generate the corresponding ketoacid. According to their stereoselectivity, those enzymes that only oxidize the L-amino acids are called L-amino acid oxidases (or deaminases) while those which act only on the D-amino acids are called D-amino acid oxidases (or deaminases).

In the presence of both L- and D-amino acids, the L-amino acid oxidases (and deaminases) will oxidize only the L-amino acids, leaving the D-amino acids untouched, whereas the D-amino acid oxidases (and deaminases) will do just the opposite. Based upon this highly stereoselective nature, these enzymes have been used in combination with other enzymes or chemical reagents for the stereospecific conversion of amino acids from one enantiomer to the other. L-Amino acid deaminases (and oxidases) have been applied in combination with D-amino acid transaminases for the stereospecific conversion of L-amino acid to D-amino acids. The L-amino acid deaminase catalyzes the conversion of L-amino acids to the α-ketoacids, which feed as substrates to D-amino acid transaminases, and are thus converted the D-amino acids.

Another application involves the use of amino acid oxidase enzymes in combination with sodium borohydride. In this case, an amino acid oxidase catalyzes the stereoselective dehydrogenation of the α-amino group in an amino acid to generate an imine intermediate, which is immediately reduced back to the racemic amine or the racemic amino acid by sodium borohydride present in the system. Because the enzyme acts on only one specific enantiomer of the amino acid without affecting the other, it constantly converts this enantiomer to the racemate while allowing the other enantiomer to accumulate. The end result of this dynamic resolution is the complete conversion of the amino acid from one enantiomer to the other.

For example, the synthesis of L-proline from D-proline using D-amino acid oxidase and sodium borohydride is known. See Huh. et al., Journal of Fermentation and Bioengineering, Vol. 74, No. 3, 189–190 (1992). Similarly, the synthesis of L-pipecolic acid from D-pipecolic acid using D-amino acid oxidase and sodium borohydride also has been described. See Huh, et al., BioSci. Biotech. Biochem., 56 (12), 2081–2082 (1992). The conversion of D-alanine to L-alanine using D-amino acid oxidase and sodium borohydride and the conversion of L-Leucine to D-Leucine using L-amino acid oxidase and sodium borohydride are also known. See Hafner, et al.. Proc. Nat. Acad. Sci., Vol. 68, No. 5, 987–991 (1971).

However, the use of sodium borohydride in combination with amino acid oxidase enzymes to stereospecifically convert amino acids from one enantiomer to the other has several disadvantages that limit its industrial applications. Sodium borohydride and some of its derivatives are sensitive to water, and easily decompose in acid or neutral pH, at which the amino acid oxidase enzyme has the maximum activity and stability. For the reduction to be effective, the hydride reagent often has to be added slowly, in multiple intervals, over a long period of time, and in very large molar excess. The large excess of borohydrides often leads to rapid deactivation or destruction of the oxidase enzymes, as well as significant increase in the cost structure for a potential industrial process. Adding to the problem is that the reactions are carried out using purified enzymes, which are available only in very small quantities, and at great cost.

Thus, it would be highly desirable to provide a catalytic hydrogenation system in combination with an amino acid oxidase system to effect the stereospecific conversion of amino acids. In this new combination, the imine intermediate generated from the amino acid oxidase catalyzed dehydrogenation would be reduced back to the amino acid by catalytic hydrogenation instead of borohydride reduction. The catalytic hydrogenation system would comprise a metal catalyst and an inexpensive hydrogen donor which together would generate efficient reducing power, without harming the amino acid oxidase enzymes or, more preferably, the microorganism cells which produce these enzymes. Such a catalyst system would allow industrial scale stereospecific conversion of amino acids to their respective enantioners on a practical and cost effective basis.

SUMMARY OF THE INVENTION

The present invention provides a catalytic system combining catalytic transfer hydrogenation with amino acid oxidase (or amino acid deaminase) catalyzed oxidation reactions, and a process for stereoselectively converting amino acids from one enantiomer to the other, or from racemic mixture to the optically active isomer. The catalyst system of the present invention preferably includes: (i) a metal, metal salt, or metal complex catalyst; (ii) a hydrogen source; (iii) an enzyme capable of oxidizing said chemical compound at said chiral center, or a microorganism capable of producing an enzyme which is capable of oxidizing said chemical compound at said chiral center, and (iv) an oxidant such as oxygen. The process of the present invention includes the step of treating an amino acid with a catalyst system of the present invention.

The present invention may be used for converting optically active amino acids to their opposite stereoisomers, or transferring racemic amino acids to their optically active stereoisomers. Thus, there is provided herein a catalyst system and a process for producing D-amino acids from their corresponding L-amino acids or racemic mixtures.

In the present invention, a D-amino acid is produced by treating its corresponding L-amino acid, or a racemic mixture, with an amino acid deaminase enzyme in the presence of a metal catalyst, an oxidant, a hydrogen source and, optionally, but preferably, a buffer.

This invention also provides a method for producing a D-amino acid by treating its corresponding L-amino acid or the mixture of D- and L-amino acid with microorganism cells which produce an amino acid deaminase enzyme, in the presence of a metal catalyst, an oxidant, a hydrogen source and, optionally, but preferably, a buffer.

DETAILED DESCRIPTION OF THE INVENTION

Amino acid oxidases are a class of oxidoreductases that stereoselectively oxidize the alpha-amino group of amino acids to produce the corresponding keto acid. It is believed that the oxidation involves the enzymatic dehydrogenation of the alpha-amino group of the amino acid to form an imine intermediate, which undergoes non-catalyzed hydrolysis to yield the keto acid. The enzymatic oxidation reaction is stereoselective; thus, only the L- or D-amino acid can be oxidized by a given amino acid oxidase enzyme. The same reaction also is catalyzed by amino acid deaminase enzymes. Within a certain pH range, it is possible to subject the imine intermediate to a metal catalyzed hydrogenation reaction to regenerate the amino acid in racemic form.

It has been discovered that certain catalytic transfer hydrogenation systems may be used in combination with amino acid oxidase enzymes and amino acid deaminase enzymes without affecting their enzymatic activity and stability. Surprisingly, it also has been discovered that these metal catalyst systems are compatible with microorganism cells, including mutant strains of *E. coli*, which are capable of producing such enzymes. Thus, according to the present invention, it is possible to convert amino acids to their corresponding enantiomers by treatment with a catalyst system including a catalytic transfer hydrogenation system and a biocatalytic oxidation system, without destroying the biocatalyst.

In a preferred embodiment of the invention, ammonium formate is included in the catalyst system both as a buffer salt for the biocatalyst and as a hydrogen donor for catalytic transfer hydrogenation. The metal catalysts, in combination with ammonium formate, form hydrogen transfer systems which are compatible with the enzymes or microorganism cells. The usefulness of this invention is not limited to the stereospecific amino acid conversion reaction described above. Instead, the potential applicability of this invention is much broader. For example, because metal catalyzed hydrogen transfer hydrogenations using a proper hydrogen donor such as ammonium formate are known for the reduction of a large variety of organic chemical groups such as olefins, ketones, aldehydes, nitriles and aromatic rings, the catalyst system of this invention may be coupled with enzymes or microorganism cells which use these compounds as substrates, or produce them as products, to provide chemical and stereoselective reactions involving a large number of chemical compounds.

The catalyst system of the present invention has been applied to the conversion of L-amino acids to D-amino acids with good yield and high optical purity. The percentage enantiomeric excess (ee) of a D-amino acid produced over its corresponding L-amino acid according to the present invention may be determined by subtracting the amount of L-amino acid present from the amount of the corresponding D-amino acid present, dividing the result by the total amount of D- and L- amino acid, and multiplying by 100.

In a preferred embodiment, an L-amino acid or a racemic mixture of an amino acid is converted to a D-amino acid by treating the L-amino acid or the racemic amino acid with amino acid deaminase and ammonium formate/Pd-C according to the process of this invention. The resultant D-amino acid is recovered from the reaction to yield the D-amino acid. The D-amino acids produced according to the present invention may be isolated using procedures well known to those of ordinary skill in the art. For example, the reaction mixture is filtered or centrifuged to remove both the bio- and chemical catalyst; the filtrate or the supernatant is concentrated by vacuum distillation to a small volume; and the product is precipitated out by pH adjustment and further purified by recrystallization. Other conventional amino acid isolation methods can be applied, such as extracting the product solution with a proper water immiscible organic solvent, including n-butanol, or passing the product solution through an ion-exchange column.

In a preferred embodiment, the catalyst system of this invention includes a buffer. Suitable buffers for use in the present invention include, but are not limited to, those which are effective in a pH range of about 5.0 to about 8.0, including ammonium formate, sodium or potassium phosphates, tris(hydroxymethyl)aminomethane hydrochlorides (TRIS Hcl), and mixtures thereof. Preferably, the buffer is ammonium formate.

In another preferred embodiment, the catalyst system of the present invention includes a microorganism capable of producing an enzyme that is capable of oxidizing a chiral center of a chiral chemical compound. In this embodiment, a catalyst system is provided without the need to isolate the oxidase enzyme. Preferably, the metal catalyst and the microorganism cells are compatible in that neither has a significant detrimental effect on the activity of the other.

The enzymes which may be used in the present invention preferably include those which are compatible with the metal catalyst system of this invention. Exemplary enzymes include amino acid oxidase enzymes, amino acid deaminase enzymes, which are generally available commercially, and mixtures thereof. For example, both D- and L-amino acid oxidases from several different origins can be purchased from Sigma-Aldrich Fine Chemicals. The choice of enzymes to be used in the process of this invention will depend upon the particular stereospecific reaction desired. For example, where it is desired to convert an L-amino acid to a D-amino acid, the preferred enzyme is an L-amino acid oxidase or deaminase.

Microorganism cells which may be used in the present invention preferably include those which produce the desired enzyme and are compatible with the metal catalyst system of this invention. More preferably, the microorganism cells are *E. coli* cells which produce the desired enzyme. In a particular preferred embodiment, the cells are *E. coli* cells which produce an L-amino acid deaminase enzyme. A strain of *E. coli* which produces an L-amino acid deaminase enzyme can be prepared by introducing into the cells a plasmid bearing the gene which encodes for synthesis of L-amino acid deaminase. A plasmid bearing such a gene can be prepared as described in U.S. Pat. No. 5,728,555, the disclosure of which is hereby incorporated by reference herein.

The metal catalysts which may be used in the present invention preferably include those which are compatible with the enzymes and microorganism cells of this invention. Exemplary metal catalysts include palladium on carbon (Pd-C), palladium on barium sulfate, palladium black, and mixtures thereof. Preferably, the metal catalyst is palladium on carbon.

The oxidants which may be used in the present invention include atmospheric oxygen, hydrogen peroxide, NAD, and mixtures thereof. Preferably, the oxidant is atmospheric oxygen.

The hydrogen sources which may be used in the present invention include ammonium formate, sodium formate, triethylammonium formate, $H_2$, and mixtures thereof. Preferably, the hydrogen source is ammonium formate.

When ammonium formate is used as a hydrogen source and a buffer, preferably the concentration of ammonium formate is about 0.1 M to about 3.0 M.

The process of the present invention may be carried out at temperature and pH ranges within which the catalyst and enzymes are stable. The preferred temperature range is about 15° C. to about 40° C. More preferably, the temperature range is about 20° C. to about 37° C. The preferred pH range is about 5.0 to about 8.0, more preferably about 6.0 to about 7.0.

The concentration of metal catalyst that provides a catalytic amount of the catalyst in the process of this invention will depend upon the particular metal catalyst employed, and preferably is in a range of about 1.0 mole % to about 100 mole %, based upon the weight of the reactant. The preferred concentration range for the palladium on carbon catalyst is about 10 mole % to about 50 mole %.

An especially preferred catalyst system has a ratio of palladium on carbon catalyst to substrate between about 0.001 to 1.0 and about 0.1 to 1.0.

The concentration of enzyme or microorganism cell that provides a catalytic amount of a desired enzyme in the process of this invention preferably is in a range of about 0.001 weight % to about 10.0 weight %, based upon the weight of the total reaction mixture. The most preferred concentration range for the enzyme or microorganism cells is about 0.01 weight % to about 1.0 weight %, based upon the weight of the total reaction mixture.

The concentration of buffer that may be used in the present invention is that which will maintain the pH of the reaction at about 5.0 to about 8.0. Preferably, the buffer will be present in an amount effective to maintain the pH of the reaction at about 6.0. This can be accomplished, for example, by using an effective amount of a 1.0 molar ammonium formate buffer.

The examples that follow are intended as illustrations of certain preferred embodiments of the invention, and no limitation of the invention is implied.

EXAMPLES

Example 1

Preparation of BioChem Catalyst

The microorganism strain *Escherichia coli* NS3302 containing amino acid deaminase enzymes was constructed and maintained in our laboratories as described in U.S. Pat. No. 5,728,555. Production and Fermentation of Strain NS3302 was carried out following a standard two-stage protocol as follows.

The colonies of strain NS3302 were inoculated from a petri-dish into a 2800 ml Fernbach flask containing 1 L of the following growth medium:

| | |
|---|---|
| Potassium phosphate (dibasic) | 13 g |
| Potassium phosphate (monobasic) | 2 g |
| Ammonium phosphate | 4 g |
| Ferric ammonium citrate | 0.24 g |
| Yeast Extract | 2 g |
| Magnesium sulfate | 1 g |
| L-isoleucine | 0.5 g |
| L-leucine | 0.5 g |

-continued

| | |
|---|---|
| L-valine | 0.5 g |
| Water | 930 ml |

After sterilization the following components were added:

| | |
|---|---|
| Glucose (50% w/v stock) | 70 ml |
| Chloramphenicol | 0.01 g |

The flask was incubated on a shaker incubator at 30° C. with agitation. The strain was grown to 1000–1900 Klett units and was used to inoculate the fermentor. The fermentor was a Biolafitte 78-100 (St. Gemainen Laye, France) 20 L. The fermentor was operated under the following conditions:

| | |
|---|---|
| Agitation | 500 rpm |
| Temperature | 30° C. |
| Back Pressure | 0.7 Bar |
| pH (maintained with NH$_3$) | 7.2 |
| Aeration | 1 vvm |
| Set Volume | 11 L |
| Inoculation | 50 ml |
| Run Time | 19 hr |

The fermentation medium was made up of the following components, per liter, unless otherwise noted:

| | |
|---|---|
| Magnesium sulfate (7.H$_2$O) | 5.35 g |
| Ferric ammonium citrate | 0.13 g |
| Potassium phosphate (dibasic) | 4.6 g |
| Manganese sulfate | 0.023 g |
| Potassium iodide | 0.74 mg |
| Nickel sulfate | 0.74 mg |
| Antifoam (Mazur Mazu DF204) | 0.4 ml |
| Yeast Extract | 10 g |
| L-isoleucine | 0.5 g |
| L-leucine | 0.5 g |
| L-valine | 0.5 g |
| Cobalt sulfate | 0.054 mg |
| Sodium molybdate(2H$_2$O) | 0.054 mg |
| Cupric sulfate | 0.088 mg |
| Zinc chloride | 0.428 mg |
| Tap water | 11 L |

Prior to inoculation, glucose was added to achieve a concentration of 25 g/L. After the initial glucose was completely depleted, glucose was fed at a variable rate to achieve less than 1 g/L for the remaining time, for a total of 512 g added. The final volume in the tank was 11.4 L. Production of the amino acid deaminase enzyme was temperature induced in the final 3 hours of the fermentation. Induction temperature was 42° C. and started after the culture reached 35 OD (Spectronic 20 Genesys by Spectronic Instruments).

After the 3 hour temperature induction, the cells were cooled to 15° C. and harvested by ultrafiltration using a DC-10 Amicon labscale ultrafiltration unit and a 500 molecular weight cut-off AG technology size 9-E. The concentrated cells, containing about 125 g dry cells per liter, were stored at 4° C. and used directly as the catalyst for the biotransformation reactions.

Example 2

Conversion of L-Phenylalanine to D-Phenylalanine

L-Phenylalanine (20 mg) was dissolved in 2.0 ml of 1 Molar aqueous ammonium formate solution, which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Phenylalanine content by chiral thin layer chromatography. The results of the analysis are set forth in Table 1.

TABLE 1

Conversion of L-Amino Acids to D-Amino Acids

| L-Amino Acid | Approximate yield of D-amino acid (%) | Approximate enantiomeric excess (%) |
|---|---|---|
| Phenylalanine | 60 | 99 |
| Valine | 50 | 65 |
| Nor-Valine | 90 | 99 |
| Leucine | 90 | 99 |
| Nor-Leucine | 85 | 99 |
| Iso-Leucine | 60 | 50 |
| Tyrosine | 90 | 90 |
| Tryptophan | 95 | 95 |
| Methionine | 90 | 99 |

As Table 1 shows, the catalyst system of this invention was used to convert numerous L-amino acids to their respective enantiomers. The stereospecificity of each reaction is indicated by the enantiomeric excess. The results show that the invention was effective for the conversion of all of the L-amino acids listed in Table 1, except L-Valine (ee 65%) and L-Iso-Leucine (ee 50%). All of the other L-amino acids were converted to their respective D-enantiomers with an enantiomeric excess of at least 95%.

Example 3

Conversion of L-Valine to D-Valine

L-Valine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Valine content by chiral thin layer chromatography. The results of the analysis are set forth in Table 1.

Example 4

Conversion of L-Tyrosine to D-Tyrosine

L-Tyrosine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Tyrosine content by chiral thin layer chromatography. The results of the analysis are set forth in Table 1.

Example 5

Conversion of L-Tryptophan to D-Tryptophan

L-Tryptophan (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Tryptophan content by chiral thin layer chromatography. The results of the analysis are set forth in Table 1.

Example 6

Conversion of L-Methionine to D-Methionine

L-Methionine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Methionine content by chiral thin layer chromatography. The results of the analysis are set forth in Table 1.

Example 7

Conversion of L-Nor-Leucine to D-Nor-Leucine

L-Nor-Leucine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Nor-Leucine content by chiral thin layer chromatography. The results of the analysis are set forth in Table 1.

Example 8

Conversion of L-Nor-Valine to D-Nor-Valine

L-Nor-Valine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Nor-Valine content by chiral thin layer chromatography. The results of the analysis are set forth in Table 1.

Example 9

Conversion of L-Leucine to D-Leucine

L-Leucine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Leucine content by chiral thin layer chromatography. The results of the analysis are set forth in Table 1.

Example 10

Conversion of L-Iso-Leucine to D-Iso-Leucine

L-Iso-Leucine (20 mg) was dissolved in 2.0 ml of 1 Molar aqueous ammonium formate solution which was adjusted to pH=6.0 with formic acid. Twenty mg of 5% palladium on carbon (wet, 50% water) was added, and the suspension was incubated with 0.1 ml of the catalyst system prepared according to Example 1. The resultant reaction mixture was stirred continuously and maintained at 30° C. for 16 hours while exposed to air. The reaction product was centrifuged and the supernatant was analyzed for D-Iso-Leucine content by chiral thin layer chromatography. The results of the analysis are set forth in Table 1.

Other variations and modifications of this invention will be obvious to those skilled in the art. This invention is not limited except as set forth in the claims.

What is claimed is:

1. A process for stereoselectively inverting a chiral center of a chemical compound, comprising the steps of:

forming a mixture of said chemical compound, an enzymatic system comprising an enzyme selected from the group consisting of amino acid oxidase, amino acid deaminase, amino acid dehydrogenase and mixtures thereof, and a metal catalyst;

stereoselectively dehydrogenating a group attached to said chiral center with said enzymatic system in the presence of an oxidant to produce a dehydrogenated group; and hydrogenating said dehydrogenated group with said metal catalyst in the presence of a hydrogen source to stereoselectivity invert the chiral center of the chemical compound.

2. A process of claim 1, wherein said metal catalyst is selected from the group consisting of palladium on carbon, palladium black, palladium on alumina, and mixtures thereof.

3. A process of claim 1, wherein said metal catalyst is palladium on carbon.

4. The process of claim 3, wherein said enzyme is an L-amino acid deaminase enzyme.

5. The process of claim 4, wherein said chemical compound having a chiral center is selected from the group consisting of L-phenylalanine, L-valine, L-tyrosine, L-tryptophan, L-methionine, L-nor-leucine, L-nor-valine, L-leucine, and L-iso-leucine, derivatives thereof, and mixtures thereof.

6. The process of claim 5, wherein said oxidant is atmospheric oxygen.

7. The process of claim 6, wherein said hydrogen source is selected from the group consisting of ammonium formate, $H_2$, cyclohexene, and mixtures thereof.

8. The process of claim 7, wherein said hydrogen source is ammonium formate.

9. The process of claim 8, wherein said catalyst system further comprises a buffer.

10. The process of claim 9, wherein said buffer is selected from the group consisting of ammonium formate, potassium phosphate, tris(hydroxymethyl)aminomethane, and mixtures thereof.

11. The process of claim 10, wherein said buffer is ammonium formate.

12. The process of claim 11, wherein said process is carried out at a pH of about 5.0 to about 8.0.

13. The process of claim 12, wherein said process is carried out at a temperature of about 15.0° C. to about 40° C.

14. The process of claim 13, wherein the concentration of said ammonium formate is about 0.1 M to 3.0 M.

15. The process of claim 14, wherein the ratio of said palladium on carbon catalyst to substrate is between about 0.001 to 1.0 and about 0.1 to 1.0.

16. The process of claim 15, further comprising recovering a D-amino acid or a protected derivative thereof from the reaction mixture.

17. The process of claim 1, wherein said dehydrogenation step produces an achiral center.

18. A process for stereoselectively inverting a chiral center of a chemical compound, comprising the steps of:

forming an aqueous reaction mixture comprising a chemical compound having a chiral center; an enzyme selected from the group consisting of amino acid oxidase, amino acid deaminase, amino acid dehydrogenase, and mixtures thereof; and a catalytic amount of a metal hydrogenation catalyst; and providing an oxidant and a hydrogen source to said reaction mixture to enzymatically and stereoselectively oxidize said chemical compound at said chiral center in the presence of said oxidant and then to catalytically hydrogenate the oxidized compound in the presence of said hydrogen source in order to stereoselectively invert the chiral center of the chemical compound.

19. A process of claim 18, wherein said metal catalyst is selected from the group consisting of palladium on carbon, palladium black, palladium on alumina, and mixtures thereof.

20. A process of claim 18, wherein said metal catalyst is palladium on carbon.

21. The process of claim 20, wherein said enzyme is an L-amino acid deaminase enzyme.

22. The process of claim 21, wherein said chemical compound having a chiral center is selected from the group consisting of L-phenylalanine, L-valine, L-tyrosine, L-tryptophan, L-methionine, L-nor-leucine, L-nor-valine, L-leucine, and L-iso-leucine, derivatives thereof, and mixtures thereof.

23. The process of claim 22, wherein said oxidant is atmospheric oxygen.

24. The process of claim 23, wherein said hydrogen source is selected from the group consisting of ammonium formate, $H_2$, cyclohexene, and mixtures thereof.

25. The process of claim 24, wherein said hydrogen source is ammonium formate.

26. The process of claim 25, wherein said catalyst system further comprises a buffer.

27. The process of claim 26, wherein said buffer is selected from the group consisting of ammonium formate, potassium phosphate, tris(hydroxymethyl)aminomethane, and mixtures thereof.

28. The process of claim 27, wherein said buffer is ammonium formate.

29. The process of claim 28, wherein said process is carried out at a pH of about 5.0 to about 8.0.

30. The process of claim 29, wherein said process is carried out at a temperature of about 15.0° C. to about 40° C.

31. The process of claim 30, wherein the concentration of said ammonium formate is about 0.1 M about 3.0 M.

32. The process of claim 31, wherein the ratio of said palladium on carbon catalyst to substrate is between about 0.001 to 1.0 and 0.1 to 1.0.

33. The process of claim 32, further comprising recovering a D-amino acid, or a protected derivative thereof, from the reaction mixture.

34. The process of claim 20, wherein said microorganism cells are a strain of *E. coli*.

35. A process for stereoselectively inverting a chiral center of a chemical compound, comprising the steps of:

forming an aqueous reaction mixture comprising a chemical compound having a chiral center, microorganism cells capable of producing an enzyme selected from the group consisting of amino acid oxidase, amino acid deaminase, amino acid dehydrogenase, and mixtures thereof; and a catalytic amount of a metal hydrogenation catalyst; and providing an oxidant and a hydrogen source to said reaction mixture to enzymatically and stereoselectively oxidize said chemical compound at said chiral center in the presence of said oxidant and then to catalytically hydrogenate the oxidized compound in the presence of said hydrogen source in order to stereoselectively invert the chiral center of the chemical compound.

* * * * *